United States Patent
Schneider et al.

(10) Patent No.: US 9,155,520 B2
(45) Date of Patent: Oct. 13, 2015

(54) ULTRASOUND PROBE FOR LAPAROSCOPY

(76) Inventors: Caitlin Marie Schneider, Vancouver (CA); Septimiu E. Salcudean, Vancouver (CA); Robert N. Rohling, Vancouver (CA); Christopher Yee Chaung Nguan, Vancouver (CA)

(*) Notice: Subject to any disclaimer, the term of this patent is extended or adjusted under 35 U.S.C. 154(b) by 484 days.

(21) Appl. No.: 13/525,183

(22) Filed: Jun. 15, 2012

(65) Prior Publication Data

US 2013/0338505 A1     Dec. 19, 2013

(51) Int. Cl.
| | |
|---|---|
| *A61B 9/00* | (2006.01) |
| *A61B 17/00* | (2006.01) |
| *A61B 8/12* | (2006.01) |
| *A61B 8/00* | (2006.01) |
| *A61B 6/00* | (2006.01) |

(52) U.S. Cl.
CPC ............... *A61B 8/12* (2013.01); *A61B 8/4218* (2013.01); *A61B 8/4455* (2013.01); *A61B 6/5247* (2013.01)

(58) Field of Classification Search
USPC ........ 600/109, 11.8, 137, 173–174, 189, 105, 600/114–118, 139, 444, 439, 459; 601/1–3; 606/169, 130, 205–213
See application file for complete search history.

(56) References Cited

U.S. PATENT DOCUMENTS

| | | | | |
|---|---|---|---|---|
| 5,383,883 | A  * | 1/1995 | Wilk et al. | 606/169 |
| 6,371,973 | B1 * | 4/2002 | Tepper | 606/205 |
| 6,589,164 | B1 * | 7/2003 | Flaherty | 600/121 |
| 8,012,092 | B2 * | 9/2011 | Powers et al. | 600/439 |
| 2003/0135091 | A1 * | 7/2003 | Nakazawa et al. | 600/113 |
| 2004/0171935 | A1 * | 9/2004 | Van Creveld et al. | |
| 2009/0036913 | A1 * | 2/2009 | Wiener et al. | 606/169 |
| 2009/0318756 | A1 * | 12/2009 | Fisher et al. | 600/109 |
| 2010/0312151 | A1 * | 12/2010 | Makin et al. | 601/2 |
| 2010/0324458 | A1 * | 12/2010 | Okada et al. | 601/2 |
| 2011/0263983 | A1 * | 10/2011 | Peszynski | 600/443 |
| 2012/0010506 | A1 * | 1/2012 | Ullrich | 600/440 |
| 2012/0035473 | A1 * | 2/2012 | Sanghvi et al. | 600/439 |
| 2012/0089029 | A1 * | 4/2012 | Harhen | 600/462 |
| 2012/0108979 | A1 * | 5/2012 | Franklin et al. | 600/463 |
| 2012/0143172 | A1 * | 6/2012 | Oko et al. | 606/1 |

* cited by examiner

*Primary Examiner* — Nicholas Evoy
*Assistant Examiner* — Lawrence Laryea (57) ABSTRACT

An intra-operative ultrasound probe for use with a robotic and laparoscopic surgical systems that allows for direct surgeon control over the position and orientation of the ultrasound image is presented. The transducer is designed to interface with the laparoscopic grasper so that it is easy to pick up in a locking, self-aligning and repeatable manner. The transducer is tracked in space using either forward kinematics or electromagnetic sensing, allowing multiple 2D images to be combined in order to create 3D ultrasound volumes. The 3D volumes can be further processed and displayed on the surgeon's console, or used to register and display acquired preoperative images at the correct spatial location within the patient.

7 Claims, 9 Drawing Sheets

ULTRASOUND PROBE FOR LAPAROSCOPY

FIELD OF THE INVENTION

The present invention relates to the integration of ultrasound into a surgical robotic system, and is useful during minimally invasive procedures.

BACKGROUND OF THE INVENTION

Minimally invasive surgery ("MIS") minimizes the overall trauma of a surgery by performing the procedure through small incisions in the abdominal wall. In comparison to traditional open surgical techniques, MIS offers the patient minimal tissue damage, reduced recovering time and quicker return to normal activities.

One type of MIS is laparoscopy, in which the surgeon performs the operation through small incisions into the abdominal, thoracic or pelvic cavities. Long instruments and a camera are inserted through these incisions and grant the surgeon access to the patient's internal organs with much reduced trauma to the body. An absorbable gas, such as carbon dioxide is used to distend the patient's cavity and provide a larger working space. Many types of surgical procedures can be performed with this method, including nephrectomy, prostatectomy and hysterectomy.

The introduction of robotic laparoscopic techniques has allowed surgeons greater dexterity by increasing the number of degrees of freedom available inside the body. Some robotic systems also include a stereo camera system, meaning the surgeon can see his/her tools and the anatomy in three dimensions, thus regaining depth perception. During robotic surgery, though, the operating surgeon is further separated from the patient and must rely on assistants to interact with the patient. Assistants perform such tasks as passing in suture, controlling suction or controlling an external laparoscopic ultrasound transducer.

Ultrasound is currently used during liver resection to localize and stage the lesions as well as determine the extent of the resection required. Similarly, ultrasound is used during partial nephrectomy to determine the resection margins and identify proper blood flow through the kidney after the tumour is removed. There have also been reports of the use of ultrasound for prostate surgery.

Ultrasound is a user dependent imaging modality, meaning that more experienced ultrasonographers are often able to create better, more informative images than those created by a less experienced user, because the positioning of the transducer imaging region is crucial to the understanding of the underlying anatomy. In addition, hand-eye coordination allows the person holding the ultrasound transducer to better correlate the image shown on the machine with its location in relation to the patient and other anatomy. Unfortunately, during laparoscopic surgical procedures and in particular during robotic laparoscopic procedures, the ultrasound transducer is often controlled by an assistant. This causes additional confusion as the ultrasound operator must position the ultrasound transducer to image tissue that is manipulated (retracted, cauterized, cut, sutured etc.) by the surgeon, and must follow the surgeon's verbal instructions or anticipate the surgeon's needs. This is clearly difficult and limits the use of intra-operative ultrasound.

With more advanced laparoscopic ultrasound techniques, ultrasound could be used more extensively in more procedures, increasing the amount of information available to the surgeon. This additional information could increase the surgeon's efficacy and efficiency as well as the patient's safety.

BRIEF SUMMARY OF THE INVENTION

This patent application describes an intra-operative ultrasound transducer for use during robotic and laparoscopic procedures.

The invention consists of the ultrasound transducer with an approximately cylindrical body containing the ultrasound transducer array and a mechanical interface located on its proximal end. The interface is designed to create a repeatable, lockable and self-aligning relationship with a robotic or laparoscopic grasping instrument. In some embodiments of the invention, the grasping interface is detachable.

In this embodiment of the mechanical interface, the grasper is oriented such that its jaws close over the probe, on the proximal side of the probe, nearest to the cable connection. The jaws of the grasper interact with mechanical stops on the grasping interlace, which, once engaged, prevent the grasper from dropping the probe.

In various embodiments of the probe, it can be tracked in physical space using robotic forward kinematics, electromagnetic sensors contained within the probe housing, or optical markers visible to a camera on the external surface of the probe housing.

In various embodiments of the invention, the collected three dimensional ultrasound data can be displayed to the surgeon in to the correct position and orientation with respect to the probe housing, either as a two dimensional image, panorama image or a volume. The data can be reconstructed into a volume that can be displayed to the surgeon using standard rendering techniques. Displays could include B-mode, Doppler, or segmented features.

The information displayed to the surgeon may contain register pre-operative images and volumes, such as computed tomography scans or magnetic resonance scans.

BRIEF DESCRIPTION OF THE DRAWINGS

In the accompanying drawings, which illustrate one or more exemplary embodiments:

FIG. 2 illustrates several detailed views of the grasping interface.

DETAILED DESCRIPTION OF THE EMBODIMENTS OF THE INVENTION

Detailed descriptions of embodiment of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner. Prior disclosure of descriptions of the embodiment of the invention was made in the publication Caitlin Schneider, Julian Guerrero, Christopher Y. Nguan, Robert Rohling, Septimiu E. Salcudean: Intra-operative "Pick-Up" Ultrasound for Robot Assisted Surgery with Vessel Extraction and Registration: A Feasibility Study", was made in the $2^{nd}$ International Conference on Information Processing in Computed Assisted Interventions", page 122-132, Jun. 22, 2011, the entirety of which is hereby incorporated by reference.

Figure 1:
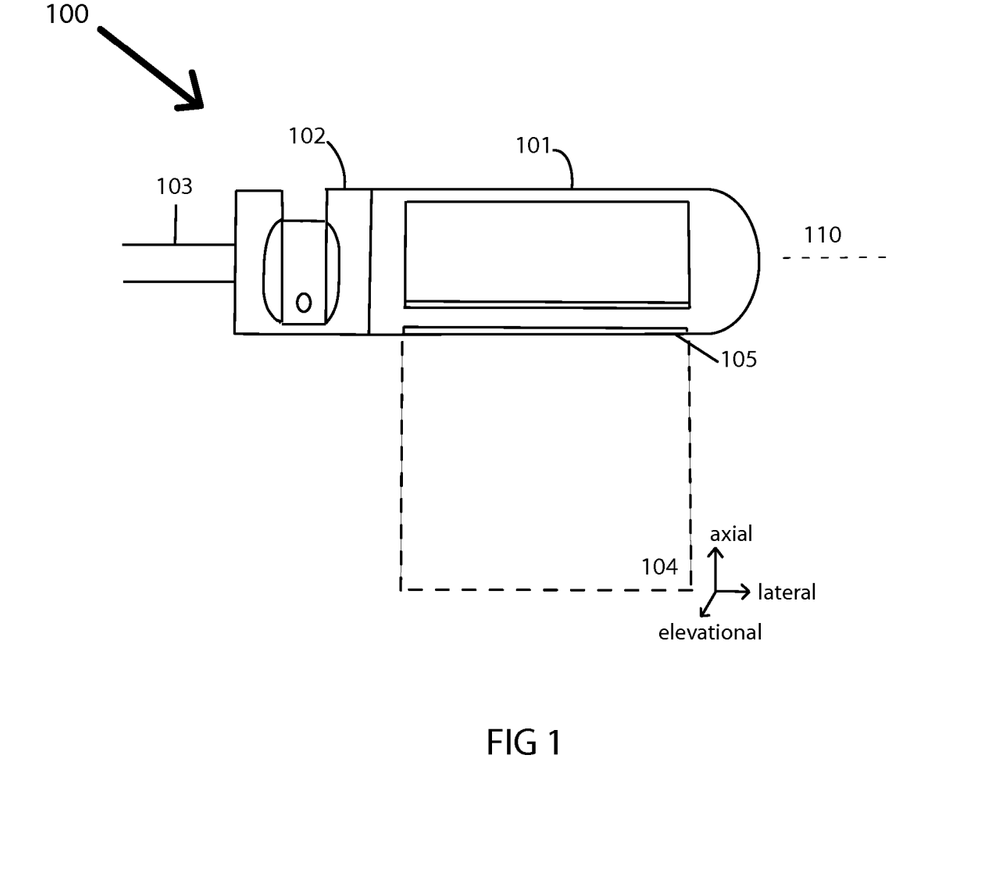
FIG. 1 illustrates the main sections of the probe in a side view

FIG. 1 shows a side view of an intra-operative ultrasound probe 100. There are three main sections of the ultrasound probe 100 including as shown an probe housing 101, a grasping interface 102, and a cable 103. For simplicity, a ultrasound linear transducer is shown, but it is possible to apply this idea to curvilinear or phased array transducers. The elongated shape of the probe housing 101, is selected for it to be easily inserted through a small incision into the body, and the cylindrical shape shown is only for illustration purposes and illustrative of a preferred embodiment. Any other shape that has a small cross-section can be used for the probe housing 101. The grasping interface 102 is preferably placed at the proximal end of the probe housing, where proximal refers to the direction closer to the cable 103, and distal refers to the direction away from the cable 103.

The cable 103 conveys the electrical signals to and from the ultrasound probe 100. In the embodiment shown, the longitudinal axis 110 of the ultrasound probe is parallel to the ultrasound probe transducer array 105 that is imaging a region of interest 104 and is parallel to the direction of the cable 103 as it connects to the probe housing 101 through the grasping interface 102.

The placement of the grasping interface 102 at the proximal end of the probe housing 101 reduces the torque needed to overcome the weight and pull of the cable 103 while moving the ultrasound probe 100.

Figure 5:
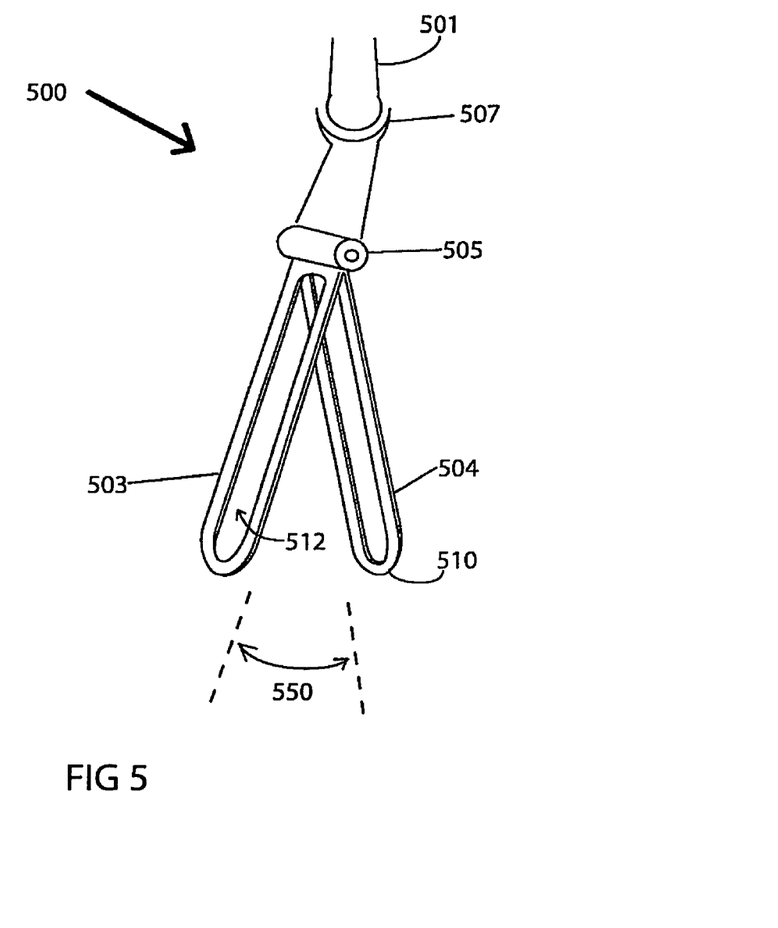
FIG. 5 illustrates one type of tool that can be used to grasp the probe.

In one embodiment of the invention, the grasping interface 102 is meant to be used with a grasping instrument such as the one shown in FIG. 5. The grasping interface 102 allows for the ultrasound probe 100 to be grasped by a robotic or laparoscopic grasping tool 500, where a grasping tool 500 is defined as having a first and second grasping jaws 503, 504 in an opposed facing relationship, with a variable grasping angle 550 between the grasping jaws 503, 504. The grasper shown schematically in FIG. 5 is similar to Intuitive Surgical's Pro-Grasp™ surgical instrument. It is desirable, although not required, for the grasping interface 102 to have no aspects that protrude past the outer diameter of the probe housing. This provides the most safety for the patient, as the ultrasound probe will not be able to catch on tissue while in use in the body.

The grasping interface 102 has two important functions which are enabled by this invention. The first function is to enable easy pick-up and release of the ultrasound probe 100 by a grasping instrument such as the instrument 500. The second function is to provide a single self-aligning configuration of the ultrasound probe 100 and therefore transducer image 104 with respect to the grasping instrument 500 as the grasping instrument 500 doses, so that the position and orientation between the grasper 500 and the grasper interface 102 is pre-defined to one and only one configuration once the grasping interface 102 is grasped by the grasper 500. Because the ultrasound array 105 is in a fixed spatial location (by location of one object with respect to the other we mean both position and orientation) relative to the grasping interface 102, once the grasper interface 102 is in its pre-defined location, then the ultrasound transducer image 104 is also in a pre-defined location relative to the grasping interface 102 and the grasper 500. The location of the ultrasound transducer image 104 relative to the grasping interface can be calibrated by known techniques such as those presented by [Mercier, L. et al., "*A Review of Calibration Techniques for Freehand 3D Ultrasound Systems*". Ultrasound in Medicine and Biology, vol. 31, pp 143-165 (2005)], such that the transformation between the grasper location and the ultrasound image location is constant and known at all times while the ultrasound probe 100 is being grasped by the grasper 500 using the grasping interface 102. The manner in which the easy pick-up and release functions and the self-aligning function are insured by this invention will be described next.

Figure 2A:
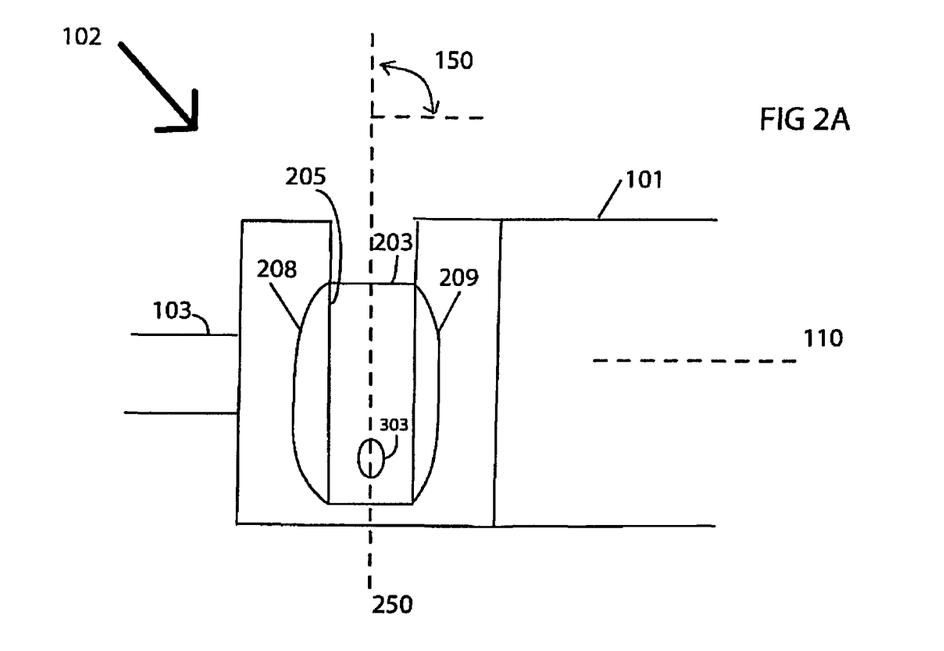
FIG. 2A is a side view of the grasping interface with a grasping angle of 90 degrees.

In one embodiment of the invention, as shown in FIG. 2A, a grasping interface 102 is shown that is orthogonal to the longitudinal axis 110 of the ultrasound probe 100, near the proximal end of the ultrasound probe 100. In order to grasp the grasping interface 102, the surgeon approaches the grasping interface 102 with the grasper 500 so that its grasping jaws 503, 504 are open to a large or maximum angle and such that the plane formed by the grasping jaws 503, 504, is roughly orthogonal to the axis 110 of the ultrasound probe. This approach direction can be seen in FIG. 3A, which shows a cross-section through plane 250 (FIG. 2A) of the grasping interface 102 as it is being approached by the grasper 500 and its grasper jaws 503 and 504, with FIG. 3B showing the grasper 500 with grasping jaws 503, 504, fully locked to the grasping interface 102, in a manner that will be described below.

Figure 2B:
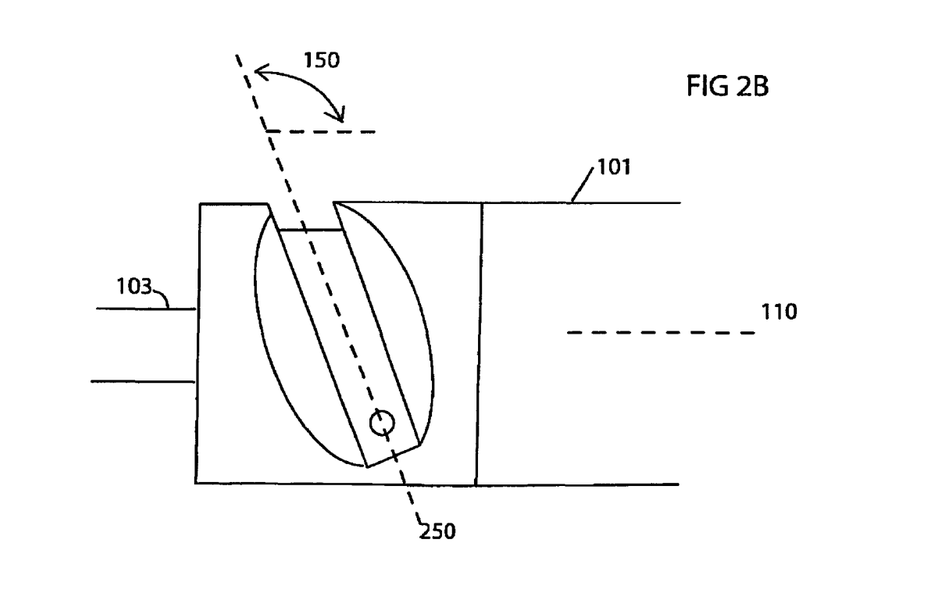
FIG. 2B is a side view of the grasping interface with a grasping interface of greater than 90 degrees but less than 160 degrees.
Figure 2C:
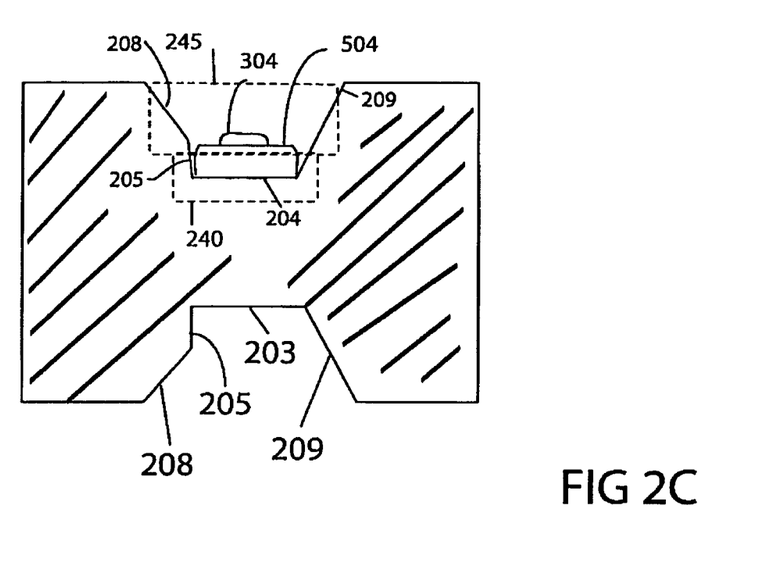
FIG. 2C is a cross-sectional view of the interface with the grasper engaged.

FIG. 2A, FIG. 2C, FIG. 3A and FIG. 3B show the grasping interface to have a grasping plane 250 that is orthogonal to the longitudinal axis 110 of the ultrasound probe 100, as shown in FIG. 2C. However, as shown in FIG. 2B, it is also possible for the grasping interface to be slanted, so that the approach by the grasper 500 to grasp the interface 102 will be with the grasping jaws 503, 504 in a plane that is at an angle 150 with respect to the ultrasound transducer longitudinal axis 110. The orthogonal orientation of the grasper interface, with angle 150 equal to 90 degrees, shown in FIG. 2 has certain advantages. These include the large orientation range that can be achieved by the ultrasound transducer axis without mechanical interference with the grasper supporting shaft 501. For example, with wristed instruments such as Intuitive Surgical's Pro-Grasp™ graspers, the orthogonal orientation of the grasping interface 102 allows the surgeon to rotate the ultrasound probe 100 with the full range of motion of the wrist joint 507, while preventing inadvertent damage to the transducer array 105. This joint typically rotates the plane formed by the grasper jaws 503, 504. This orthogonal orientation also provides an easy method for grasping. Indeed, as the grasper 500 attempts to grasp the grasping interface 102, there will be a reaction force due to the ultrasound probe 100 lying on the tissue from where it needs to be picked-up. This reaction force helps push the grasper interface 102 against the open grasper jaws 503, 504, as the grasper closes. The grasper 500 envisioned for use with this ultrasound probe allows for approximately 90 degrees of motion in the pitch and yaw directions. With the grasping jaw 503, 504 orthogonal to the longitudinal axis 110 of the ultrasound probe 100 and cable 103, the maximum range of motion of the grasper 500 is possible before there is interference between the grasper 500 and the cable 103.

Figure 3A:
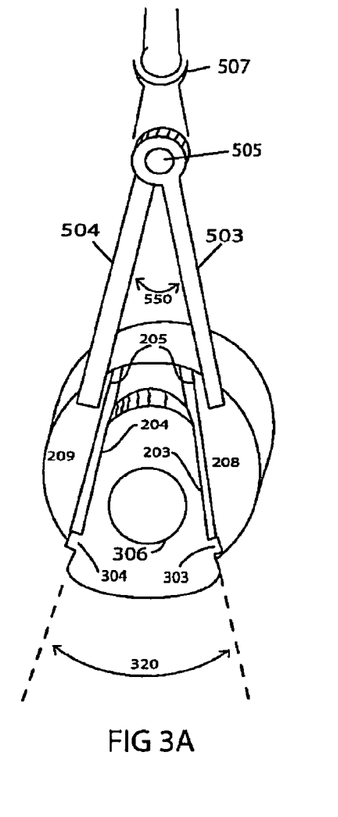
FIG. 3A is an axial cross-sectional view of the interface with the grasper in the unlocked position.
Figure 3B:
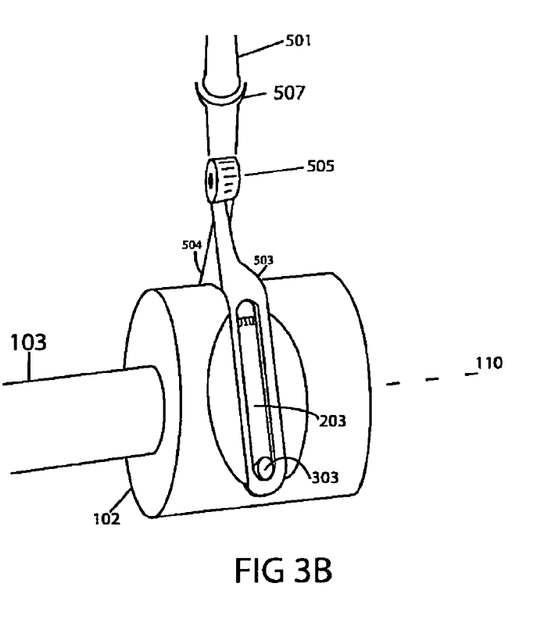
FIG. 3B is an isometric view of the interface with grasper engaged in the 'locked' position.

FIG. 2A, FIG. 3A and FIG. 3B illustrate an embodiment of the grasping interface which has two channels 203 and 204, which are designed to mate with the grasper jaws 503 and 504, respectively. By designed to mate, we mean that the channel 203 matches grasper jaw 503 within a small tolerance such that, when grasper jaw 503 is fully bottomed out in channel 203, grasper jaw 503 can slide along the channel direction but cannot rotate in the channel because of the channel constraints. The same holds for the channel 204 grasper jaw 504 pair. Furthermore, the two channels 203 and 204 can be designed to "jointly mate" with the grasper jaws 503 and 504 when the variable angle 550 between the grasper jaws of the grasper 500 is equal to the fixed or "locking angle" 320 between the channels 203 and 204. When the grasper variable angle 550 is equal to the locking angle 320, then by pushing the grasper towards the channels, with the grasper oriented in such a manner that the grasp jaw 503 faces channel 203 and grasper jaw 504 faces channel 204, then the grasper 500 and the grasping interface 102 can be mated so that each grasper jaw 503, 504 matches respective channels 203, 204, and the only motion that can exist between the grasper 500 and the grasping interface 102 is a translation as a result of the grasper "pinching" away the V-channel made by the two channels 203 and 204.

To prevent such pinching motion, a locking mechanism can be devised so that the pinching motion is prevented, i.e. so that the sliding between the channels 203 and 204 and the grasper jaws 503, 504 is stopped. One embodiment of such a locking mechanism is shown in FIG. 2A, FIG. 2B and FIG. 3A, FIG. 3B, and makes use of central slots 512 in jaws 503, 504. As the grasper jaws 503 and 504 close into the channels 203, 204, the mechanical stops 303, 304 fit inside the central grasper jaw slots 512, preventing the grasper jaws from sliding off the grasping interface 102. Clearly the mechanical stops 203, 204 must be narrower than the central jaw slot 512 width. A round peg is shown in this embodiment to match the shape of rounded grasper tip 510.

The channels 203 and 204 have directions that span a plane which we have called the locking plane, and which is shown as 250 in FIG. 2A and FIG. 3B.

The mechanism by which a surgeon would approach the grasping interface 102 with the grasper 500 is by aligning the plane of the grasper jaws 503, 504 with the grasping plane of channels 203, 204, approaching the V formed by the two channels with the open grasper, pushing the grasper past the limits stops, the fully closing the grasper jaws 503 and 504 over the matching channels 203, 204. As the grasper closes, the grasping interface is pinched outwards from the grasper 500 and the limits stops of the channels engage the slots of the grasping jaw. When the channel mechanical stops 303 and 304 have bottomed out, then the grasper will be at the locking angle, therefore each grasper jaws 503, 504 will be bottomed out into the channels 203, 204. This perfectly jointly matched configuration between the grasper jaws and the channels do not allow any motion of the grasper interface 102 relative to the grasper jaws 503, 504. Indeed, grasper translation along the ultrasound transducer axis 110 is blocked by the channel edges, translation in the plane orthogonal to this axis is locked by the grasper pinching motion against the mechanical limit stops 303, 304, rotation about the transducer axis 110 is blocked by the pinching of the channels 203, 204 with the grasper 500, and rotation about axes orthogonal to the ultrasound transducer axis are blocked by the fitting match between the grasper jaws 503, 504 and the channels 203, 204. Therefore pinching action of the grasper jaws 503, 504 over opposed outwardly facing channels 203, 204 with limit stops 303, 304, results in a pre-defined position and orientation of the grasper 500 with respect to the grasper interface 102.

By choice of the channel and channel wall geometry, it is clear that even if the V formed by the matching channels 203 and 204 is not oriented to perfectly match the grasper angle of approach in the grasping plane, the grasping motion will align this V to match the grasper even when substantial angular misalignment exists. The effect of other misalignment errors can be mitigated by designing the channels 203, 204 to have tapered walls 208, 209, shown in the cross section of the channel 203 in FIG. 2C.

Preferably, in order to combine the robustness of the grasping interface to misalignment with the ability to grasp the grasping interface with very little play between the two, the channel cross-section profile can be made to have a low-profile portion 240 that tightly matches the cross-section width of the grasper jaws 503, 504 when they are approaching the locking angle or when they bottom out, together with wider and smaller angle tapered channel 245 that has the role of "capturing" the grasper jaws as they close towards their matching channels.

The tapered walls 208, 209 improve self alignment properties of the grasping interface 102, but also allow the ultrasound probe 100 to be easily released. In the event that both 208 and 209 and were vertical, the grasping jaws 503, 504 would have a tendency to jam in between the walls, or else they are too loose to hold the ultrasound probe 100 tight. The one short less tapered wall 205 does help hold the ultrasound probe against the interface when torque is applied to the probe housing 101.

In one preferred embodiment, the grasping interface 102 is made of a hardened material such as hardened stainless steel with the dual goal of protecting the ultrasound probe 100 from the grasping jaws 503,504, but allows the grasping jaws 503, 504 to slip on the channel bottom 203 and help the grasper 500 to be placed correctly in the grasping interface 102. The probe housing 101 can be made from many standard plastics, and both materials can be sterilized.

When used with a robotic laparoscopic system, the grasper 500 that picks up the ultrasound probe 100 will allow the surgeon greater dexterity in controlling the motion of the ultrasound probe 100 as well as placing it in the appropriate place to achieve the most informative image possible. Advantageously, the surgeon will be able to control the ultrasound probe 100 him or herself, increasing the effectiveness of the imaging by allowing direct hand-eye-coordination, rather than directing an assistant.

The locked orientation of the ultrasound probe 100 and grasper 500 allows for a method of tracking using the kinematics of a robot manipulator. Because the transformation between the tool position and the ultrasound image has been previously calibrated, the ultrasound image position can be known. In addition to using the robot kinematics for tracking, electromagnetic ('EM') sensing can be employed. An EM sensor 470 is embedded in the probe housing 101 which allows it to be tracked relative to an electromagnetic transmitter outside of the patient's body 750. This becomes important if, during the procedure the ultrasound probe 100 cannot be easily seen in the laparoscope 720. The EM sensor 470 can be used to determine the ultrasound probe location to prevent the surgeon spending time finding a 'lost' instrument.

FIGS. 3A and 3B illustrates the grasping interface 102, in cross sectional view and an isometric view respectively. The view in FIG. 3A looks in the proximal direction, towards the cable 103. The central cable lumen 306 can be seen as a conduit for the connections between the cable 103 and the transducer array 105. The grasper 500 in this figure is in the unlocked position, such that it is poised to grab the grasping interface 102. FIG. 3B illustrates the grasper 500 and grasping interface 102 in the locked position, in which the tool jaws 503, 504 are engaged with the channel 203, 204 and the mechanical stops 303, 304.

The angle between the channels 203, 204 on each side of the grasping interface 102, is determined by the tool jaw 503 length.

Although the embodiment shown in the figures uses a rounded tip grasper with a planar grasping jaw, the various embodiments of the invention may include grasping interfaces that can be used with graspers not of the exact shape shown in FIG. 5. Other such graspers could have curved grasping jaw, curved either in towards each other, creating pincher like graspers, or curved in the direction normal to the opposing jaws, creating angled graspers. The grasping interface 102 could also include different methods of limit stop implementation. In the figures, a round peg is depicted, but the limit stop is any method of stopping the graspers from sliding in the channels 203, 204 of the grasping interface 102. Such other limit stops may include short protrusions from the channel bottom that hold the side of the jaw closest to the hinge 505 from slipping out of the interface. Alternatively, the channel floor, could be shaped to hold the grasping jaw using slight depressions, or in the case of a curved pincher like grasper, be curved to match the approximate curvature of the grasping jaw.

The grasping interface 102 can also be detachable, not permanently mounted to the probe housing 101. A set screw can be used to hold the grasping interface 102 to the probe housing 101. In this way, the grasping interface 102 can be removed and replaced. Alternatively, the grasping interface 102 does not entirely encircle the cable 103, allowing easier removal. In the event that the section of the grasping interface 102 collinear with the transducer array is open, the interface can be removed from the ultrasound probe 100 and replaced with one designed for a different set of graspers.

Figure 4A:
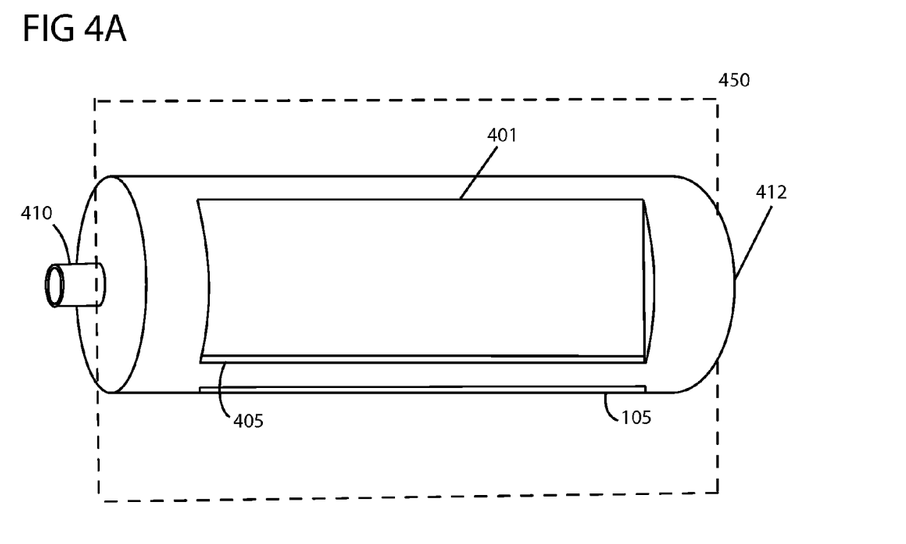
FIG. 4A illustrates the exterior probe housing in detail.

FIG. 4A illustrates in detail the probe housing 101. The probe housing 101 is approximately cylindrical with a rounded front end 412. Two attachment landings 401 are cut into the housing 101 at angles approximately equal to those of the channels 203, 204 of the grasping interface 102. On the lower side of the landing 401, close to the transducer array 105, a narrow groove 405 for the attachment 600 is cut horizontally inward. These grooves 405 (one on each side of the probe housing 101) and attachment landings 401 are designed to fit with an attachment 600 such as that seen in FIG. 6. This type of attachment could be used for the placement of visible markers used for image based tracking techniques, or alternative grasping sites for tools that do not match the general description of the grasper 500, or an assistants tool.

Figure 4B:
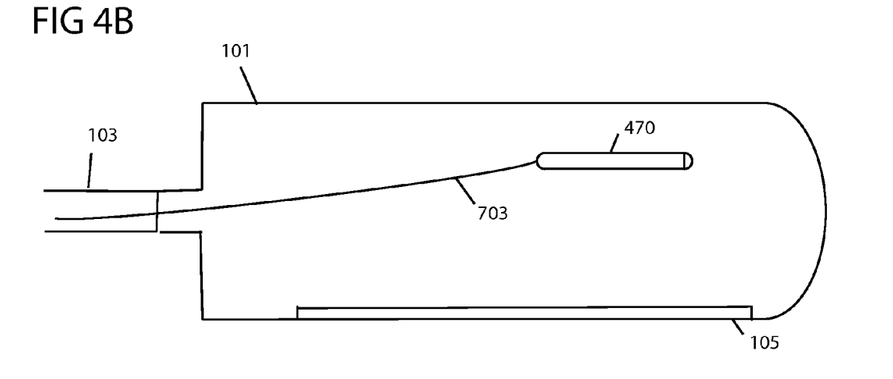
FIG. 4B is a longitudinal cross-section showing one embodiment of possible embedded electromagnetic tracking sensor.

FIG. 4B shows a cross-sectional view of the probe housing 101, as defined by the plane 450. The embedded EM sensor 470 can be visualized.

The probe housing 101 is attached to the grasping interface 102 by means of a cable lumen connection 410.

Figure 6:
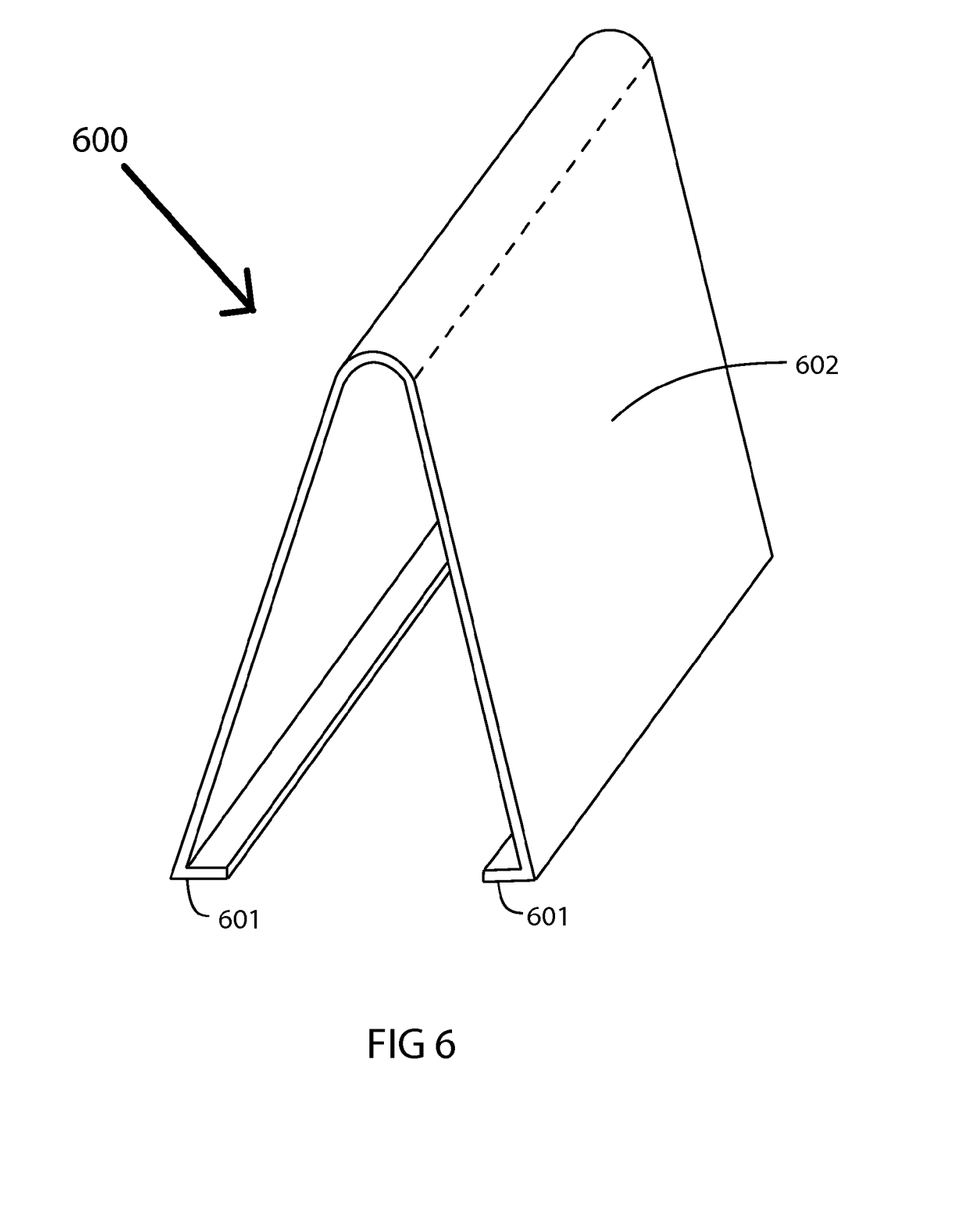
FIG. 6 illustrates the optional attachment to the probe housing.

FIG. 6 illustrates an example of an attachment 600 to fit over the probe housing 101. The skies of the attachment 602 mimic the angle between the attachment landings 401 of the probe housing 101. The lip of the attachment 601 on the open side of the attachment 600 will fit in to the narrow groove 405 on the probe housing 101.

Figure 7:
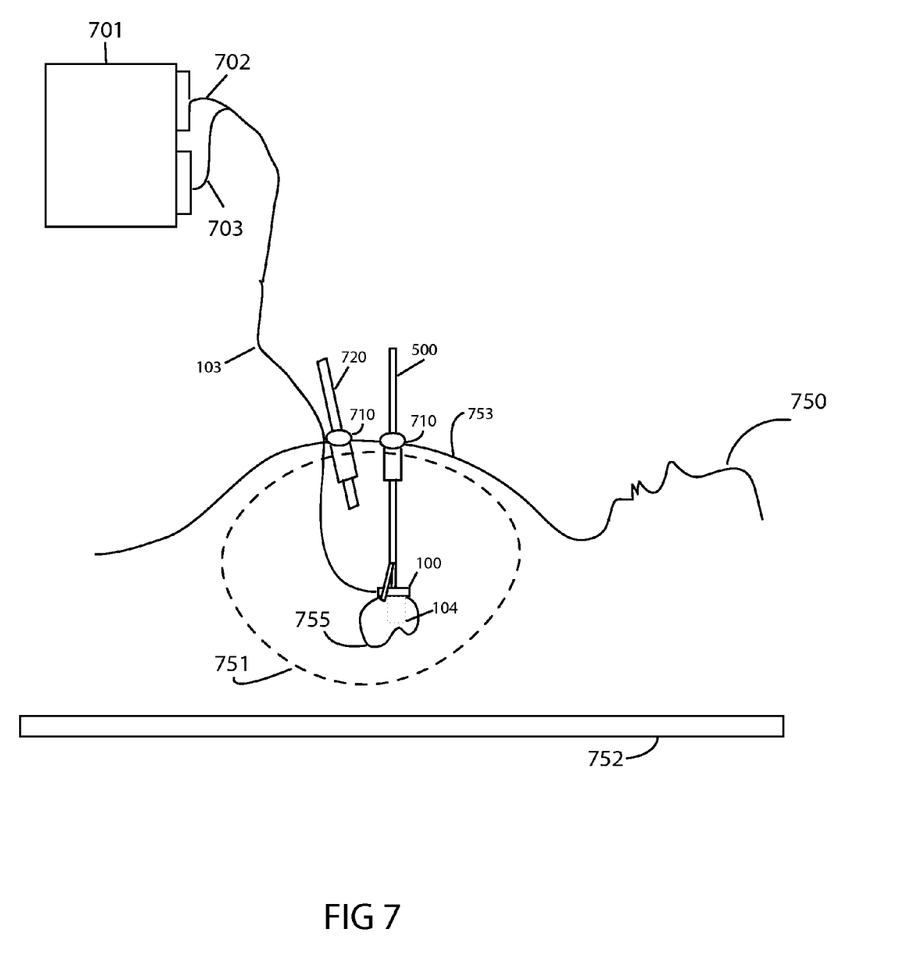
FIG. 7 is a general operating set-up, including robotic system, patient and ultrasound probe.

FIG. 7 demonstrates the general operational set-up for this invention. The patient 750 would typically be lying on an operating room table 752. The patient's abdomen is insufflated to create an operating space in the abdominal cavity 751, this involves creating positive pressure in the patient's abdominal cavity by filling the cavity with an inert gas, typically carbon dioxide. Several incisions are made in the abdominal wall 753, through which a cannula 710 is placed. A cannula is a long hollow tube through which instruments such as a grasper 500 or a laparoscope 720 can be passed. The laparoscope 720 is the camera that is used in laparoscopic minimally invasive surgery to allow the surgeon to see inside the patient's abdominal cavity 751. In various embodiments of the invention, the laparoscope 720 can be monocular or stereoscopic. The ultrasound probe 100 will be placed through an incision but outside the cannula lumen. This means that no extra incision is needed in the patient's abdominal wall 753, but the ultrasound probe 100 can be available to the surgeon throughout the entire procedure. In some embodiments of the invention, the ultrasound probe 100 can be passed through the cannula 710. The probe is grasped and can be moved throughout any area of the patient's abdominal cavity 751 that can be reached by the grasper 500. When in use the surgeon will press the probe 100 against the target organ 755, such as the kidney, liver or prostate. When good acoustic coupling is achieved between the probe 100 and the target organ 755, and ultrasound image 104 can be created from the electric signals from the transducer array 105.

The cable 103 leaves the ultrasound probe 100 and connects to the ultrasound machine 701. The ultrasound machine 701 is capable of processing the electrical signals from the transducer array 105 and collecting the ultrasound data which can be processed in different ways to produce several image types, including B-mode images, Doppler images and continuous wave Doppler audio. The cable 103 carries two sets of wire, one carrying the ultrasound transducer array signals 702 and one carrying the electromagnetic position sensor signals 703.

Because the ultrasound probe 100 can be tracked, it is possible to display the ultrasound data, such a B-mode ultrasound image 104 to the surgeon in its correct spatial location with respect to the ultrasound probe 100. It is also possible to combine a sequence of ultrasound data into 3D volumes. These volumes can be visualized by the surgeon through conventional rendering techniques. In some embodiment of the invention, this visualization could be accomplished through stereographic video systems and displayed through a robotic surgeon's console. The object that is visualized can be a segmented B-mode ultrasound, to show the organ surface, or a strictly Doppler segmentation, to show a skeleton structure of the vessels. This can allow the surgeon to see past the surface of the tissue and understand the underlying anatomy during the surgical procedure.

Visualization of pre-operative images, such as CT or MRI volumes, can also be provided with this invention. When the intra-operative ultrasound images 104 provided from the ultrasound probe 100 are registered to pre-operative images, such as CT or MRI, the pre-operative images can be displayed in their correct spatial location with respect to the ultrasound probe 100 and surgeons view through the laparoscope 720. Often time multiple modalities are able to highlight different features of the anatomy or the disease. For example, although prostate cancer can be identified in magnetic resonance scans, it is often difficult to identify in ultrasound scans. Thus the combination of multiple modalities is beneficial to surgical navigation. Unfortunately, the issue of multimodality registration is non-trivial. We present examples from the literature below as possible methods to complete this registration problem.

Image registration techniques can be applied to match the areas of interest such as the target organ 755, which are being scanned with the ultrasound probe 100, with that of the CT or MR scan. Once such method of registration described in [Schneider, C. M. et al., "*Intra-operative "Pick-Up" Ultrasound for Robot Assisted Surgery with Vessel Extraction and Registration: A Feasibility Study*", Proc. IPCAI, LNCS 6689, pp. 122-432] employs segmented vessels around the volume of interest. The vessels of the CT scan are segmented pre-operatively, such that a surface mesh is created. During the procedure, the vessels walls are segmented from the ultrasound image in real-time and the approximate center of the vessel in each slice was calculated. The two representations of the vessel structure are aligned with each other using point based matching such that the centers of the tube structures align. Another approach to multimodality image registration involving ultrasound uses a method of ultrasound simulation [Wein, W. et al., "*Automatic CT-ultrasound registration for diagnostic imaging and image-guided intervention.*" Medical Image Anaylsis. Vol. 12, pp 577-585, 2008]. Here ultrasound simulation is used to create an ultrasound image based on the information from the CT scan. The real-time ultrasound image and the simulated ultrasound image can then be registered more reliably with correlation based methods, since it is now a single modality registration.

Figure 8:
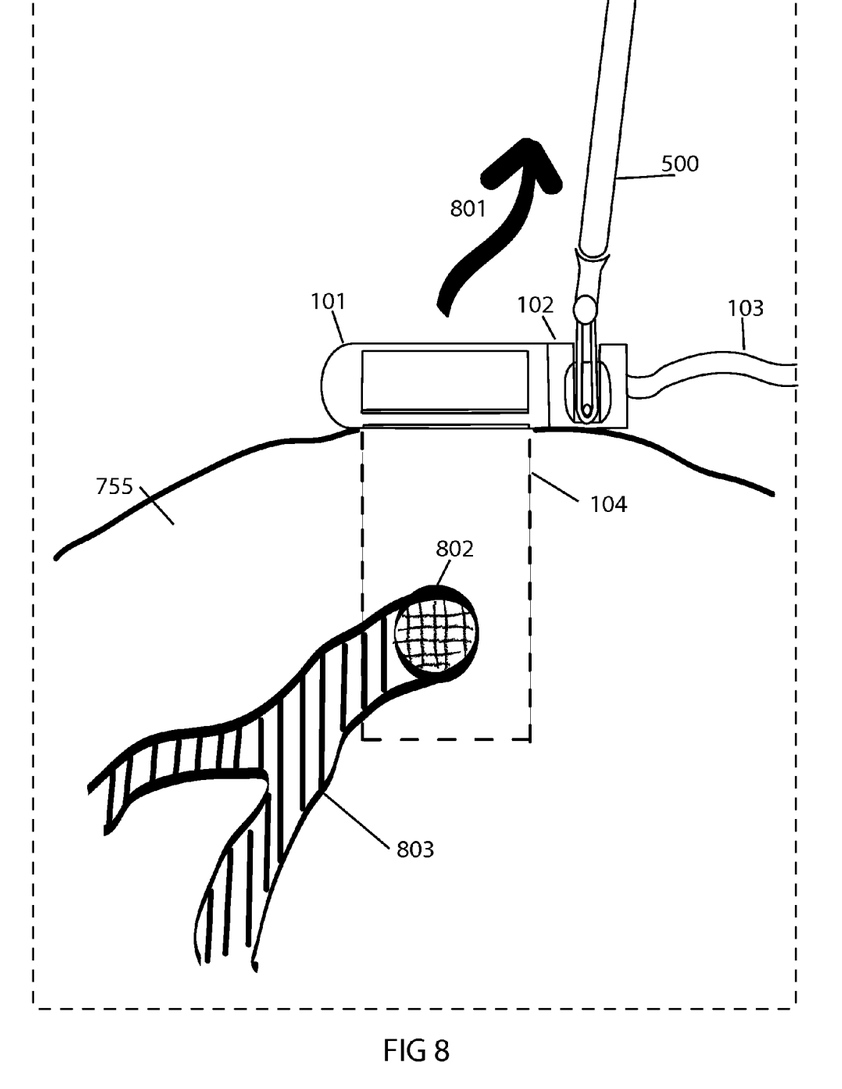
FIG. 8 illustrates one possible visualization of the ultrasound image and 3D reconstructed volume.

FIG. 8 shows an example image of what a surgeon might see during use of this invention. The grasping interface 102 is being grasped by the grasper 500. The probe housing 101 and thus the plane of the ultrasound image 104 is moved through space in a direction of motion 801. The ultrasound image 104 can be overlaid on the surgical image, to show the surgeon in the image in its proper orientation with respect to the probe housing 101. The image can be tracked through the use of the embedded EM sensor 470, optical sensing of the probe with the stereo laparoscope, or forward robot kinematics, given the known position of the grasper 500. The ultrasound images 104 can be stitched together to make a 3D volume along the direction of travel 801 if the motion is in the elevation direction (out-of-plane), or a 2D panorama image in the motion is in the lateral or axial directions (in-plane) with respect to the 2D ultrasound image 104. In both cases, the surgeon is presented with a wider view, or additional features then what would be available from a single 2D ultrasound image. In this representation, the Doppler signal was extracted from each image 802, which in this example was the cross-section of a vessel. The Doppler components of the images can be used to create a depiction of the vessel tree 803. This entire structure can be displayed to the surgeon, giving him or her a much better understanding of the underlying structures.

Moreover, while the invention has been described in connection with the above embodiment, it is not intended to limit the scope of the invention to the particular forms set forth, but on the contrary, it is intended to cover such alternatives, modifications and equivalents as may be included within the scope of the invention. Further, the scope of the present invention fully encompasses other embodiments that may become obvious to those skilled in the art and scope of the present invention is limited only by the appended claims.

What is claimed as the invention is:

1. An ultrasound probe that can be picked up and released by a grasper having first and second grasping jaws in an opposed facing relationship with a variable grasping angle between the grasping jaws, comprising
    a housing containing an ultrasound imaging array, a cable at a proximal end of said housing,
    a grasping interface at said proximal end of said housing, comprising
    first and second channels facing away from each other in opposed facing relationship to the grasping jaws, and jointly mating to the first and second grasping jaws, respectively, when the grasping angle between the first and second grasping jaw is closed to a pre-defined locking angle, thus locking the grasping interface to the grasper in a pre-defined position and orientation when the grasper is at its locking angle
    said first and second channels, in combination with said first and second grasping jaws, comprising limit stops preventing the grasping jaws from closing beyond the locking angle and slipping from said first and second channels respectively when said first and second channels are mated with said first and second jaws respectively, as the grasper is closing onto the grasping interface, and
    said first and second channels comprising tapered walls to gradually constrain said first and second grasping jaws to the grasper interface first and second channels as the angle between the grasping jaws is closed towards the locking angle.

2. An ultrasound probe as in claim 1 wherein said first channel and said second channels span a plane that crosses said cable.

3. An ultrasound probe as in claim 1 wherein said grasping interface is detachable from and lockable to said housing in order to allow graspers of different sizes or designs to be locked in a pre-defined position and orientation with respect to said housing.

4. An ultrasound probe as in claim 1, further comprising an electromagnetic sensor within the housing to independently sense the position and orientation of the probe housing with respect to a fixed coordinate system.

5. An ultrasound probe as in claim 1, further comprising optical markers on an exterior surface of the housing that that can be localized by an endoscopic camera.

6. An ultrasound probe as in claim 1, wherein said housing further comprises a landing and groove to which an attachment can be detachably mounted in a stable and repeatable manner.

7. An ultrasound probe as in claim 1, wherein said grasping interface is made of hardened stainless steel.

* * * * *